United States Patent
Munro et al.

(10) Patent No.: US 8,216,239 B2
(45) Date of Patent: *Jul. 10, 2012

(54) DEVICE FOR BONE FIXATION

(75) Inventors: Chad Richard Munro, Mabou (CA); Peter Senn, Waldenburg (CH)

(73) Assignee: Synthes USA, LLC, West Chester, PA (US)

( * ) Notice: Subject to any disclaimer, the term of this patent is extended or adjusted under 35 U.S.C. 154(b) by 311 days.

This patent is subject to a terminal disclaimer.

(21) Appl. No.: 12/613,672

(22) Filed: Nov. 6, 2009

(65) Prior Publication Data

US 2010/0063504 A1    Mar. 11, 2010

Related U.S. Application Data

(63) Continuation of application No. 10/530,087, filed as application No. PCT/CH02/00550 on Oct. 3, 2002, now Pat. No. 7,632,272.

(51) Int. Cl.
*A61B 17/58* (2006.01)

(52) U.S. Cl. ......................................................... 606/67
(58) Field of Classification Search ............... 606/62–68
See application file for complete search history.

(56) References Cited

U.S. PATENT DOCUMENTS

| 4,227,518 | A | * | 10/1980 | Aginsky | 606/63 |
| 5,356,410 | A | * | 10/1994 | Pennig | 606/62 |
| 6,077,264 | A | * | 6/2000 | Chemello | 606/67 |
| 7,632,272 | B2 | * | 12/2009 | Munro et al. | 606/67 |

* cited by examiner

*Primary Examiner* — Nicholas Woodall
(74) *Attorney, Agent, or Firm* — Fay Kaplun & Marcin, LLP

(57) ABSTRACT

A bone fixation device includes an intramedullary pin having a longitudinal axis, a proximal end, and a distal tip configured and dimensioned for insertion into a medullary canal of a bone and a bone plate disposed at the proximal end of the intramedullary pin, wherein the bone plate includes an angled tab configured and dimensioned to have a center of gravity lying on a radius of a cross-sectional area of the intramedullary pin taken orthogonally to the intramedullary pin's longitudinal axis.

20 Claims, 3 Drawing Sheets

DEVICE FOR BONE FIXATION

PRIORITY CLAIM

The present application is a Continuation of Application of U.S. patent application Ser. No. 10/530,087 filed on Jan. 30, 2006 which is a National Phase Application of PCT Patent Application Serial No. PCT/CH2002/000550 filed on Oct. 3, 2002.

FIELD OF THE INVENTION

The invention relates to a bone fixation device, in particular for fixing fractures at the proximal femur.

BACKGROUND OF THE INVENTION

In the case of fractures at the proximal femur, especially in the case of pertrochantric fractures, medullary pins are frequently brought in to the femur for immobilizing bone fragments. Moreover, at the proximal end of the medullary pin, a bone plate is mounted, by means of which the forces and moments, acting on the head of the hip joint and the greater trochanter, can be transferred to the medullary pin.

U.S. Pat. No. 5,356,410 to Pennig discloses a generic device, for which a perforated bone plate, coming to rest on the greater trochanter, is fastened by means of a screw connection to the proximal end of a medullary pin without transverse boreholes. It is a disadvantage of this known device that the bone plate is disposed diametrically to the neck of the femur and protrudes distantly beyond the hip screws, which can be connected to the bone plate for immobilizing fixing the head of the hip joint.

SUMMARY OF THE INVENTION

The present invention remedies this problem. It is an object of the invention to create a device for bone fixation, especially at the proximal femur, which, on the one hand, transfers an existing muscle force over the hip screw as well as over the bone plate directly to the medullary pin and, on the other, transfers forces, acting on the head of the hip joint, not onto the bone plate and, with that, directly on to the shaft of the femur. Furthermore, the muscles, especially the vastus lateralis, the gluteaus minimus, the piriformis and the gluteaus medius and ligaments are not affected distally by the extension of the bone plate.

The inventive bone fixation device comprises essentially an intramedullary pin and a bone plate, which is intended to lie in contact with the greater trochanter and is disposed at the proximal end of the medullary pin, the latter, in its proximal half facing the proximal rear end, having at least one transverse borehole passing through it for accommodating a hip screw and the bone plate terminating proximally above this transverse borehole.

The advantages, achieved by the invention, can be seen to lie essentially therein that, due to the inventive device,

- a resistance or counter-moment can be offered to the muscle forces, which act on the greater trochanter, especially in the case of fractures of type 31 A3.2 of the AO (Association for Osteosynthesis) classification;
- forces acting on the head of the hip joint, especially the force component acting parallel to the neck of the femur can be transferred to the medullary pin; and
- the muscles and ligaments, surrounding the greater trochanter, are not affected.

The length L of the bone plate, measured parallel to the longitudinal axis of the medullary pin, preferably is between 2 mm and 40 mm.

In a preferred embodiment of the inventive device, the bone plate comprises a distally angled tab, the center of gravity of which, if projected into a cross-sectional area orthogonal to the longitudinal axis of the medullary pin, lies on a radius, which encloses an angle β of between 0°+100° and preferably of between +40° and +50°. These ranges for the angle β are for the embodiment of the inventive device at the right femur. For the embodiment of the inventive device, which can be used for the left femur, the angle β is between 0° and −100° and preferably between −40° and −50°. This arrangement permits the bone plate to be passed past muscles and ligaments disposed at the greater trochanter.

In a further embodiment of the inventive device, a further tranverse borehole for accommodating a locking screw passes through the distal half of the medullary pin facing the tip of this pin. By these means, the advantage can be attained that the load on the proximal zone of the femur is relieved and the absorption of this load is taken over by the medullary pin. Instead of the transverse borehole, transverse grooves are also possible, which are disposed transversally to the longitudinal axis of the medullary pin at the tip of latter.

In a different embodiment of the inventive device, the medullary pin and the bone plate are constructed in one piece, so that the device to be implanted comprises fewer individual parts.

In yet another embodiment of the inventive device, the tab is constructed in such a manner, that it is at a distance from the medullary pin and, viewed parallel to the longitudinal axis, is passed around the medullary pin with an angle α, the angle α being between 10° and 200° and preferably between 20° and 40°.

BRIEF DESCRIPTION OF THE DRAWINGS

The invention and further developments of the invention are explained in even greater detail below with reference to partially diagrammatic representations of several examples, where.

DETAILED DESCRIPTION OF THE PREFERRED EMBODIMENTS

Figures 1, 3:
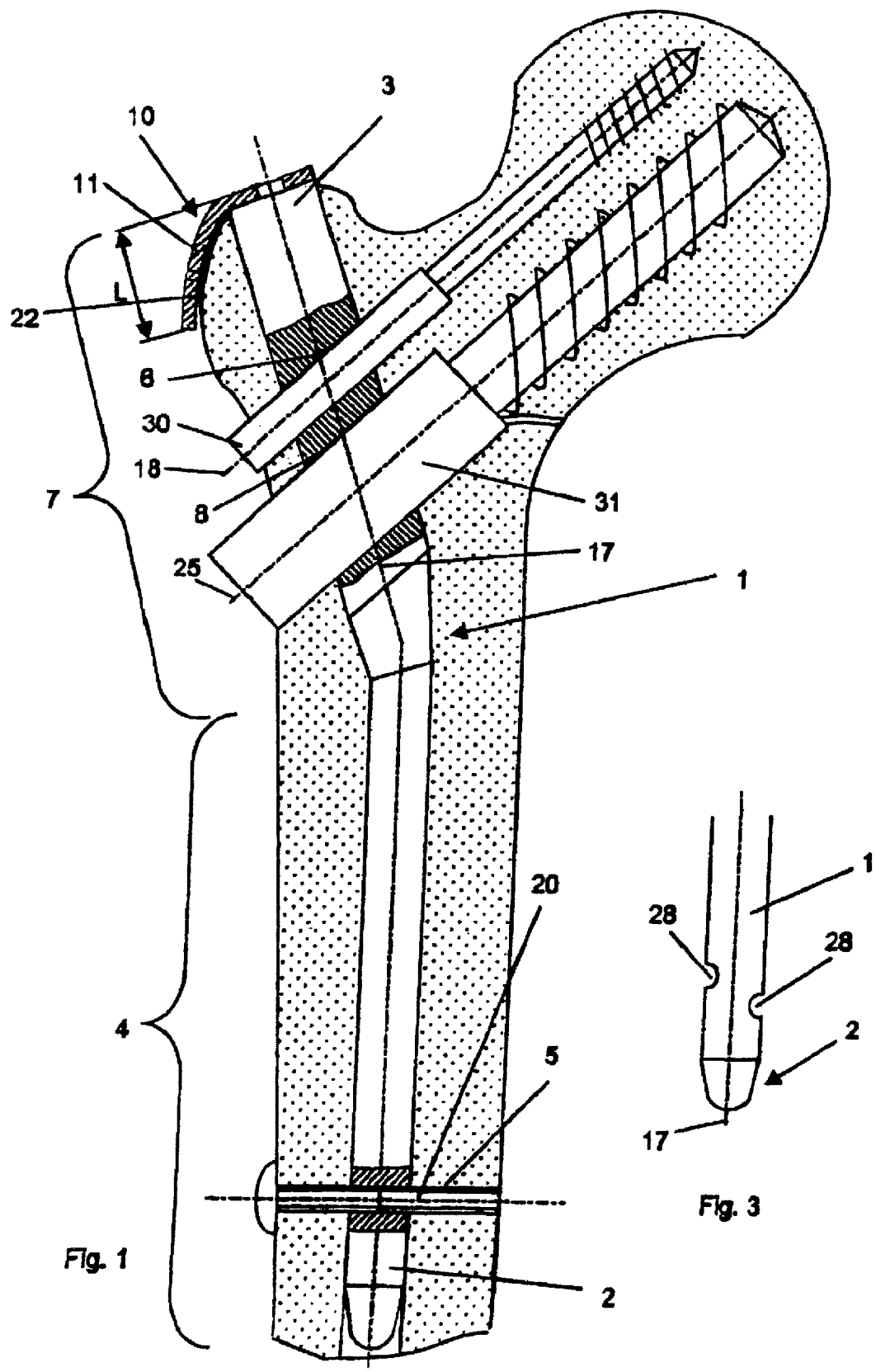
FIG. 1 shows a section through an embodiment of an inventive device at the proximal femur.
FIG. 3 shows a section of the distal portion of the medullary pin in one embodiment of the inventive device.

In*—FIG. 1, the medullary pin 1, introduced into the medullary space of a femur, is shown together with a bone plate 10, which is disposed at the greater trochanter. The medullary pin 1 has a longitudinal axis 17 and a proximal half 7 and a distal half 4 coaxial with this longitudinal axis 17. The bone plate 10 is angled distally and comprises a part, which is disposed transversely to the longitudinal axis 17 of the medullary pin 1, where the bone plate 10 is fastened by means of a screw connection 16 to the proximal rear end 3 of the medullary pin 1, and a tab 22, which extends towards the distal tip 2 of the medullary pin 1 and is provided with perforations 11. Furthermore, in its proximal half 7, the medullary pin 1 comprises a proximal transverse borehole 6 and a second transverse borehole 8, both of which are intended to accommodate hip screws 30 and 31. The transverse boreholes 6 and 8 pass through the medullary pin transversely to the longitudinal axis 17. The bone plate 10 ends proximally above the proximal transverse borehole 6. In the distal half 4 of the medullary pin 1, a transverse borehole 5 is disposed also transversely to the longitudinal axis 17 of the medullary pin 1 at the distal tip 2 of the latter. A locking screw 20 is introduced into this distal transverse borehole 5 and screwed into the femur.

Figure 2:
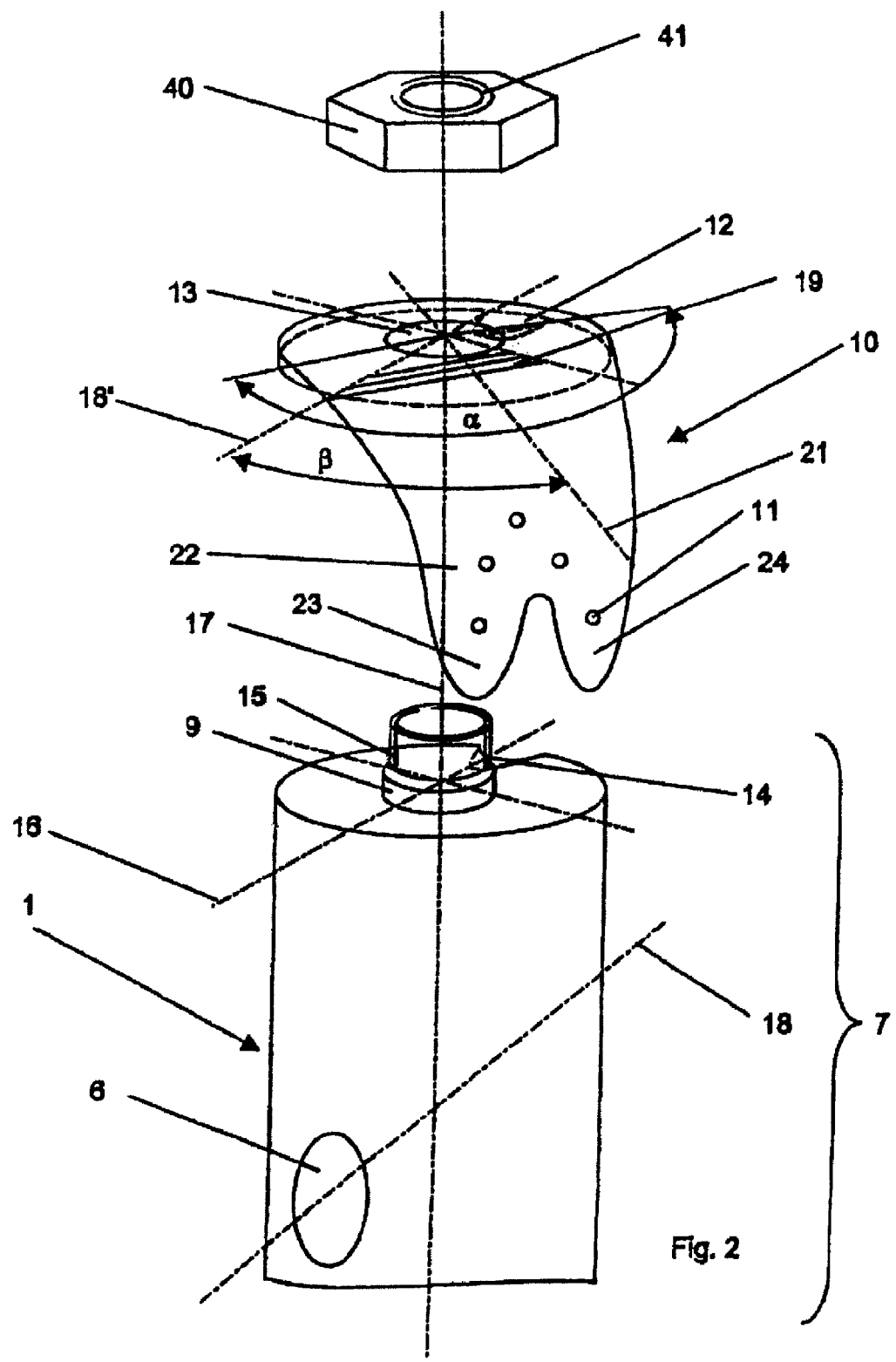
FIG. 2 shows an exploded representation of the preferred embodiment of the inventive device.
Figure 4:
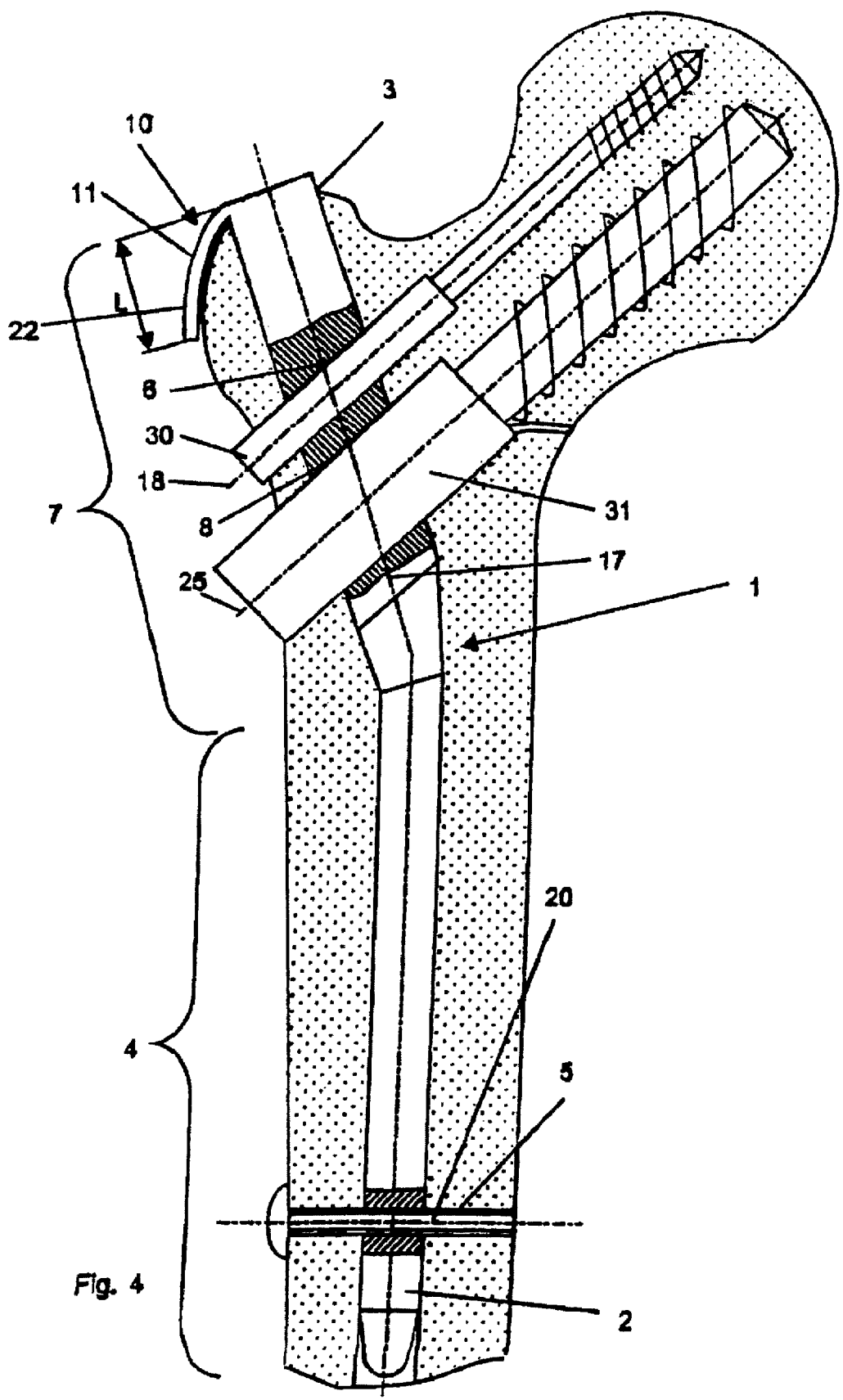
FIG. 4 shows a section through an embodiment of an inventive device at the proximal femur.

In FIG. 2, the proximal half 7 of the medullary pin 1 and the bone plate 10 are shown. The bone plate 10 comprises a part, which is disposed transversely to the longitudinal axis 17 of the medullary pin 1 and a tab 22, angled distally, with two petals 23; 24, which are aligned towards the distal tip of the medullary pin 1. In a cross-sectional area 19, orthogonal to the longitudinal axis 17 of the medullary pin 1, the projection of the center of gravity of the tab 22 lies on a radius 21, which encloses an angle β of 45° with the projection 18 of the borehole axis 18 of the proximal transverse borehole 6 in this cross-sectional area 19. Viewed parallel to the longitudinal axis 17 of the medullary pin 1, the tab 22 envelopes the medullary pin 1 at an angle a which ranges from 155° to 165°. The petals 23, 24 end proximally with respect to the proximal transverse borehole 6. Furthermore, the bone plate 10, in its part that is transverse to the longitudinal axis 17 of the medullary pin 1, comprises a circular borehole 13, which is disposed coaxially with the longitudinal axis 17 and by means of which the bone plate 10 can be pushed over a corresponding circularly cylindrical elevation 9, which is provided at the proximal rear end 3 of the medullary pin 1. At its surface facing the proximal rear end 3 of the medullary pin 1, the bone plate 10 includes a cam 12, which can be lowered into a corresponding depression 14, which is provided at the proximal rear end 3 of the medullary pin 1. By these means, the bone plate 10 can be brought into a defined position relative to the medullary pin 1 and secured against rotation about the longitudinal axis 17 of the medullary pin 1. The bone plate 10 is immobilized at the proximal rear end 3 of the medullary pin 1 by means of a nut 40, the internal thread 41 of which can be screwed over a terminal external thread 15 provided at the circularly cylindrical elevation 9 at the rear end 3 at the medullary pin 1. In another embodiment of the inventive device depicted in FIG. 4, the medullary pin 1 and the bone plate 10 are constructed as one piece so that the implanted device comprises fewer individual parts.

FIG. 3 shows a section of the distal half 4 of the medullary pin 1. The distal half 4 differs from the embodiment of the medullary pin 1 shown in FIG. 1 only therein that, instead of the distal transverse borehole 5, two transverse grooves 28, arranged in parallel, are provided. The transverse grooves 28 are disposed transversely to the longitudinal axis 17 of the medullary pin 1, extend parallel to a plane through the longitudinal axis 17 of the medullary pin 1 and the borehole axes 18 and 25 and partly accommodate locking screws 20 (FIG. 1.)

The invention claimed is:

1. A bone fixation device, comprising:
   an intramedullary pin having a longitudinal axis, a proximal end, and a distal tip configured and dimensioned for insertion into a medullary canal of a bone;
   a bone plate disposed at the proximal end of the intramedullary pin;
      wherein the bone plate includes an angled tab configured and dimensioned to have a center of gravity lying on a radius of a cross-sectional area of the intramedullary pin taken orthogonally to the intramedullary pin's longitudinal axis.

2. The device of claim 1, wherein a distal half of the intramedullary pin includes a transverse borehole passing through it for accommodating a locking screw.

3. The device of claim 1, wherein the intramedullary pin is provided with at least two transverse grooves in its distal half.

4. The device of claim 1, wherein the bone plate and the intramedullary pin are a single piece.

5. The device of claim 1, wherein a proximal half of the intramedullary pin has a transverse borehole that passes through it for accommodating a hip screw.

6. The device of claim 1, wherein the bone plate has a circular borehole and the proximal end of the intramedullary pin has a cylindrical elevation corresponding thereto, so that the bone plate may be disposed about the elevation.

7. The device of claim 6, wherein the cylindrical elevation at the proximal end of the intramedullary pin has an external thread.

8. The device of claim 7, further comprising a nut with an internal thread corresponding to the external thread.

9. The device of claim 1, wherein the bone plate has a cam that can be lowered into a depression provided at the proximal end at the intramedullary pin, so that the bone plate can be connected with the intramedullary pin in a defined relative position and secured against rotation.

10. The device of claim 1, wherein the tab, viewed parallel to the longitudinal axis, extends around the intramedullary pin at an angle α, the angle α being between 10° and 200°.

11. The device of claim 1, wherein the bone plate has at least one perforation.

12. The device of claim 1, wherein the bone plate includes a pair of petals having at least two perforations.

13. The device of claim 1, wherein:
   a distal half of the intramedullary pin includes a plurality of transverse grooves extending parallel to a plane through the longitudinal axis.

14. A bone fixation device comprising:
   an intramedullary pin having a longitudinal axis, a proximal end, and a distal end configured and dimensioned for insertion into a medullary canal of a bone; and
   a bone plate disposed at the proximal end of the intramedullary pin, the bone plate including an angled tab with a pair of petals extending toward the distal end of the intramedullary pin;
   wherein the angled tab is configured and dimensioned to have a center of gravity lying on a radius of a cross-sectional area of the intramedullary pin taken orthogonally to the intramedullary pin's longitudinal axis.

15. The device of claim 14, wherein the angled tab includes a plurality of perforations.

16. The device of claim 14, wherein the angled tab extends around the intramedullary pin over an angle of between 10° and 200° relative to the longitudinal axis.

17. The device of claim 14, wherein:
   a distal half of the intramedullary pin includes a plurality of transverse grooves extending parallel to a plane through the longitudinal axis.

18. The device of claim 14, wherein the proximal end of the intramedullary pin has an external thread.

19. The device of claim 14, further comprising a nut with an internal thread corresponding to the external thread.

20. The device of claim 14, wherein the angled tab extends around the intramedullary pin over an angle of between 20° and 40° relative to the longitudinal axis.

* * * * *

UNITED STATES PATENT AND TRADEMARK OFFICE
CERTIFICATE OF CORRECTION

| | | |
|---|---|---|
| PATENT NO. | : 8,216,239 B2 | Page 1 of 1 |
| APPLICATION NO. | : 12/613672 | |
| DATED | : July 10, 2012 | |
| INVENTOR(S) | : Munro et al. | |

It is certified that error appears in the above-identified patent and that said Letters Patent is hereby corrected as shown below:

Column 1, lines 5-9, Related U.S. Application Data, should read

--The present application is a Continuation of U.S. Patent Application Serial No. 10/530,087 filed on January 30, 2006 (now U.S. Patent No. 7,632,272), which is a National Phase application of PCT Patent Application Serial No. PCT/CH2002/000550 filed on October 3, 2002--.

Signed and Sealed this
Twenty-eighth Day of August, 2012

David J. Kappos
*Director of the United States Patent and Trademark Office*